United States Patent [19]

Kujawski

[11] Patent Number: 4,795,434
[45] Date of Patent: Jan. 3, 1989

[54] APPARATUS FOR POSITIONING A SENSOR IN VIVO

[75] Inventor: Dennis Kujawski, Nashua, N.H.

[73] Assignee: C. R. Bard, Inc., Murray Hill, N.J.

[21] Appl. No.: 95,308

[22] Filed: Sep. 10, 1987

[51] Int. Cl.$^4$ .............................................. A61M 5/18
[52] U.S. Cl. .................................... 604/159; 128/634; 128/772; 604/164
[58] Field of Search ......................... 128/748, 632–634, 128/635, 772; 604/53, 93, 117, 158–163, 164–170, 280, 283–284

[56] References Cited

U.S. PATENT DOCUMENTS

| | | | |
|---|---|---|---|
| 2,310,021 | 2/1943 | Heidbrink | 128/204.8 |
| 3,021,840 | 2/1962 | Hallamore et al. | 128/200.21 |
| 3,523,522 | 8/1970 | Whitehead et al. | 128/771 |
| 3,625,212 | 12/1971 | Rosenberg et al. | 604/52 |
| 3,766,916 | 10/1973 | Moorehead et al. | 604/167 X |
| 3,853,126 | 12/1974 | Schulte | 604/8 |
| 4,150,673 | 4/1979 | Watt | 604/408 |
| 4,219,021 | 8/1980 | Fink | 604/93 |
| 4,280,723 | 7/1981 | Moldestad | 285/376 |
| 4,417,886 | 11/1983 | Frankhouser et al. | 604/53 |
| 4,417,887 | 11/1983 | Koshi | 604/162 |
| 4,496,349 | 1/1985 | Cosentino | 604/175 |
| 4,531,937 | 7/1985 | Yates | 604/53 |
| 4,569,347 | 2/1986 | Frisbie | 604/165 X |
| 4,616,652 | 10/1986 | Simpson | 128/344 |
| 4,619,640 | 10/1986 | Potolsky et al. | 604/7 |
| 4,723,556 | 2/1988 | Susman | 128/748 |

FOREIGN PATENT DOCUMENTS

2108675 5/1983 United Kingdom ................ 128/748

Primary Examiner—Kyle L. Howell
Assistant Examiner—Angela D. Sykes
Attorney, Agent, or Firm—Wolf, Greenfield & Sacks

[57] ABSTRACT

Apparatus for positioning a sensor probe in vivo, including a probe advancement mechanism and a mating interconnection for positioning a distal end of a sensor probe a predetermined distance from the distal end of an indwelling catheter. The advancement mechanism includes a plurality of telescoping elements. The distal tip of the probe is moved from a retracted position within the advancement mechanism where the probe is maintained sterile and protected from breakage, to an advanced position wherein the distal tip of the probe is advanced through the catheter to a predetermined position with respect to the distal tip of the catheter at which the sensor measurement is made. The mating interconnection is provided between the distal end of the advancement mechanism and the proximal end of a catheter of a selected length to ensure use of the advancement mechanism only with catheters of the selected length and diameter whereby the distal tip of a probe may be precisely positioned with respect to the distal tip of the catheter. The mating interconnection is preferably a unique luer-type fitting wherein a unique female luer-type fitting in the catheter hub permits attachment to both the unique male luer-type fitting on the advancement mechanism and to a standard male luer fitting on any other device.

11 Claims, 4 Drawing Sheets

APPARATUS FOR POSITIONING A SENSOR IN VIVO

BACKGROUND OF THE INVENTION

This invention relates to apparatus for positioning a sensor in vivo, and more particularly to a probe advancement mechanism and a mating interconnection for positioning the distal end of a sensor probe a predetermined distance from the distal end of an indwelling catheter.

There are numerous medical procedures which require the precise positioning of the distal end of a sensor probe within a blood vessel or other body cavity. For example, it has been proposed to perform a blood gas analysis on hospital patients both during and after surgery by placing a probe having a blood gas sensor at its distal tip within the patient's blood vessel. The sensor may measure one or all of the partial pressures of oxygen ($PO_2$) and carbon dioxide ($PCO_2$), and the negative logarithm of hydrogen ion activity (pH), to give an indication of the patient s cardiac, respiratory and circulatory functioning, and the rate of metabolism. The sensors may be electrical, chemical, and/or optical.

Among the suggested techniques of in-vivo measurement has been the use of fiber optic probes. In a fiber optic probe, light from a suitable source travels along an optically-conducting fiber to its distal end where it undergoes some change caused by interaction with a component of the medium in which the probe is inserted or interaction with a material contained in the probe tip which is sensitive to (i.e., modified by) a component in the medium. The modified light returns along the same or another fiber to a light-measuring instrument which interprets the return light signal.

Fiber optic sensors appear to offer several potential benefits. A fiber optic sensor is safe, involving no electrical currents in the body, and the optical fibers are very small and flexible, allowing placement in very small blood vessels. The materials used, i.e., plastic, metal, and glass, are suitable for long-term implantation.

However, one of the difficulties with fiber optic sensors is the fragility of the optical fibers. The fibers must be threaded through a blood vessel or other body cavity, sometimes over long distances, without breakage of the fiber. Furthermore, the fiber tip must not injure or puncture the vessel wall. Still further, for accurate measurement with many types of blood gas sensors and other procedures, the sensor probe must be precisely positioned within the blood vessel or body cavity in order to achieve an accurate measurement.

It is an object of this invention to provide an apparatus for positioning a sensor probe in vivo at a predetermined position in the body.

Another object is to provide apparatus for advancing a sensor probe within a catheter of selected length so as to position the distal end of the probe a predetermined distance from the distal end of the catheter.

A further object is to position a probe in vivo without injuring the blood vessel or other body cavity in which the probe is positioned.

A further object is to position a probe in vivo without damage to the probe.

Still another object is to provide a system for in-vivo positioning of a probe in a catheter wherein a mating interconnection is provided between a catheter of selected length and a probe advancement means such that the probe can only be used with catheters of selected length.

SUMMARY OF THE INVENTION

According to this invention, apparatus is provided for positioning a probe in vivo. The apparatus includes a telescopic advancement mechanism positionable at the proximal end of a catheter for axially moving a probe within the catheter. The advancement mechanism includes a plurality of elements connected in telescoping relationship for advancing the probe through the catheter and positioning the distal end of the probe a predetermined distance from the distal end of the catheter. With the telescoping elements expanded, the probe is retracted within the advancement mechanism so as to maintain sterility and protect the probe for breakage. When the telescoping elements are collapsed, the probe is advanced through the catheter. Stop means are provided for limiting the relative telescoping movement of the elements for precise positioning of the distal end of the probe with respect to the distal end of the catheter.

In another aspect of this invention, a mating interconnection is provided between the proximal end of a catheter having a selected length and the distal end of a probe advancement mechanism so that the probe is used only with catheters of a selected length. In the preferred embodiment, the mating interconnection consists of a female luer fitting having an additional cylindrical bore on the catheter hub and a male luer fitting having an additional cylindrical projection, of complimentary dimensions to the female cylindrical bore, on the advancement mechanism. This unique female luer-type fitting allows connection of the catheter to either an advancement mechanism having the unique male luer-type fitting or to a standard male luer fitting, but prevents use of the advancement mechanism with a catheter not having the unique female luer-type fitting. Thus, an indwelling catheter can be used with both the probe advancement mechanism and various other devices having standard male luer fittings, while the advancement mechanism can only be used with catheters of selected length having the unique female luer-type fitting so that the probe tip is precisely positioned with respect to the catheter tip.

"Proximal" and "distal" are used herein in their ordinary sense, wherein, for example, the distal end of an indwelling catheter is the end positioned in the body furthest from the point of insertion and the proximal end is the opposite end located outside the body.

DETAILED DESCRIPTION OF THE PREFERRED EMBODIMENT

The probe advancement mechanism and mating interconnection of this invention will be described for use in positioning in a blood vessel a fiber optic probe for measuring the partial pressure of oxygen in the blood. However, it is understood that the apparatus of this invention can be used for positioning any type of probe in vivo.

Numerous types of in-vivo sensor probes are available for measuring various blood parameters, such as the concentration of gases, electrolytes, potassium, or calcium in the blood, or the pH of the blood. These sensor probes may be chemical, electrical, and/or optical. Furthermore, there are pacing electrodes available which are positionable in the heart. In addition to placing sensor probes and electrodes in vivo, the apparatus of this invention can be used for positioning any elongated cylindrical or tubular body in vivo.

Figure 1:
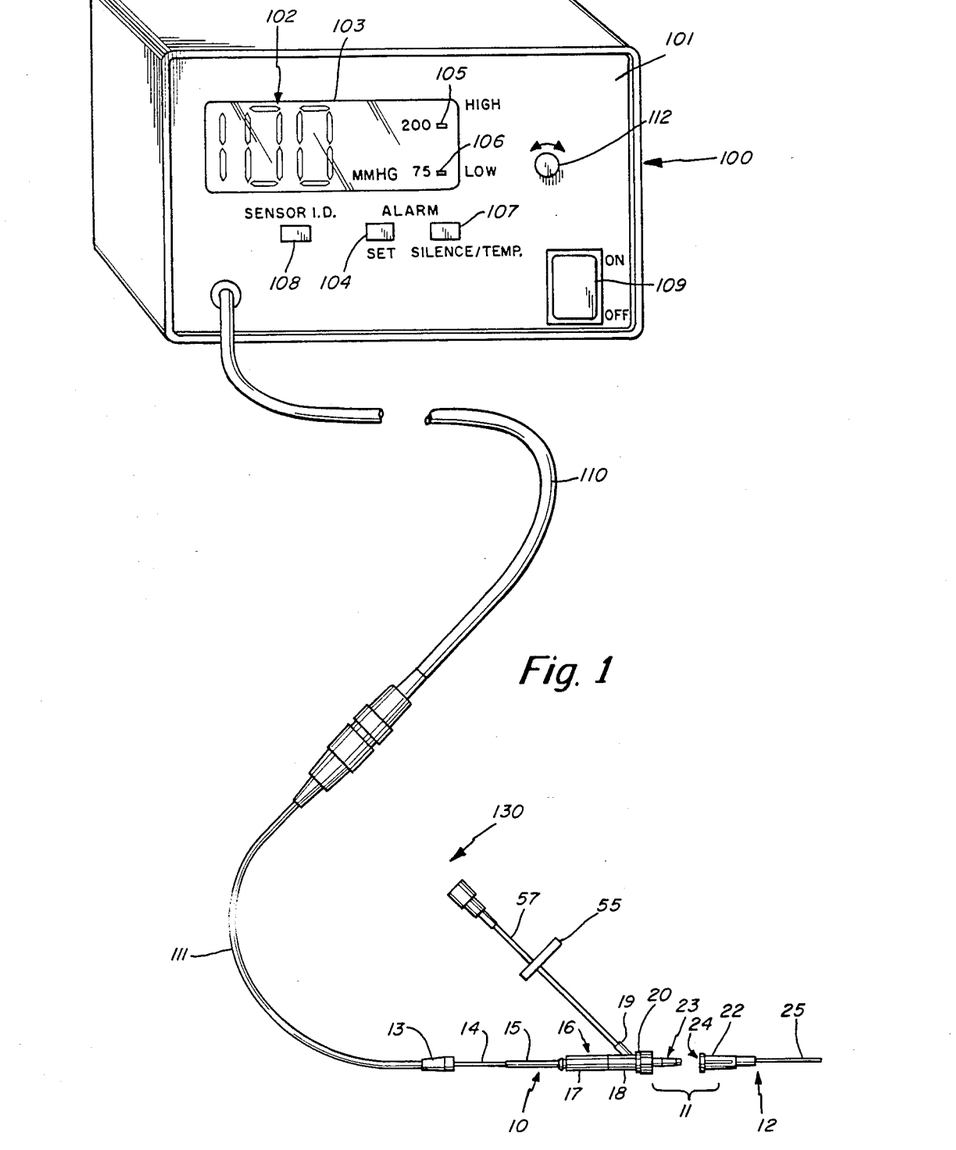
FIG. 1 is a perspective view of a blood gas monitor and blood gas sensor system incorporating the probe advancement mechanism and mating interconnection of this invention.

In the preferred embodiment shown in FIG. 1, an advancement mechanism 10 and a mating interconnection 11 of this invention are used in conjunction with a $PO_2$ blood gas monitor 100 and blood gas sensor system 130. The mating interconnection 11 is between advancement mechanism 10 and an intra-arterial catheter 12. The monitor and sensor system are intended for use in a patient whose condition requires intra-arterial cannulation and continuous or intermittent oxygen monitoring. The $PO_2$ sensor probe is designed to be placed in the radial artery (see FIG. 8) and can also provide access to the artery for blood pressure monitoring and blood sampling.

As shown in FIG. 1, the front panel 101 of the monitor gives a digital display 102 of either the partial pressure of oxygen ($PO_2$) or the temperature. Included in the display window 103 are the high and low $PO_2$ limits, e.g., 200 and 75 mmHG respectively, which are set by pushing the alarm set button 104 and turning the dial 112 to the desired numerical setting. If the blood gas measurement exceeds the high or low $PO_2$ limit, the appropriate high or low light 105 or 106 will flash and an alarm will sound. To silence the alarm, the alarm silence button 107 is pushed. The alarm silence button 107 also functions as a temperature button for displaying in the display window the temperature at which the blood gas measurement is taken. A sensor ID button 108 is provided for entering the sensor identification number located on the sensor probe. An on/off switch 109 is also provided on the front panel of the monitor.

As shown in FIG. 1, the monitor 100 is connected via a patient connector cable 110 to the sensor system. The sensor system includes a sensor assembly cable 111, the advancement mechanism 10, and the intra-arterial catheter 12, which are connected sequentially to the distal end of the patient connector cable, and a $PO_2$ sensor probe which is axially movable within these elements. The mating interconnection 11 is provided at the distal end of the advancement mechanism 10 and at the proximal end of the catheter 12.

Figure 2:
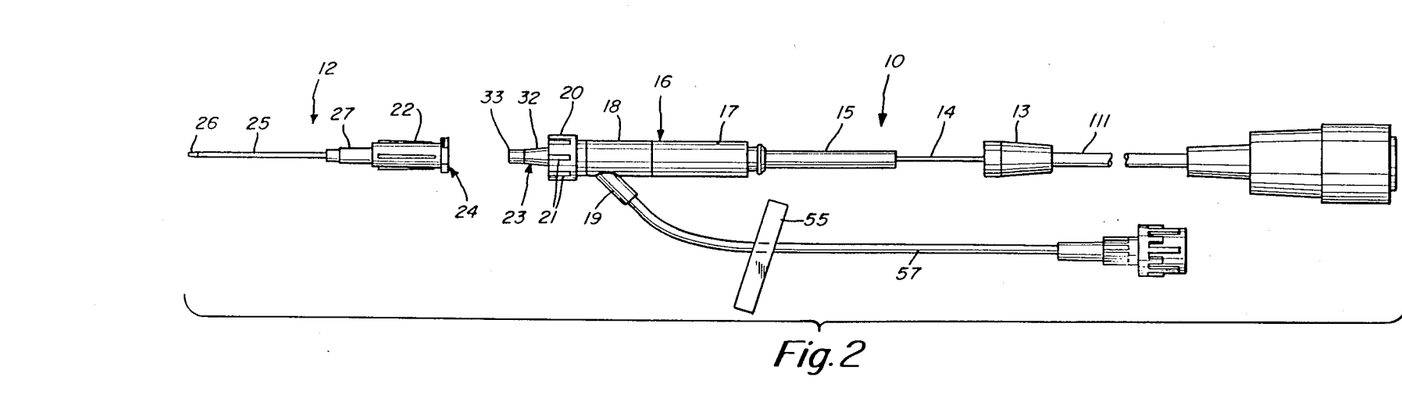
FIG. 2 is a full-size side, elevational view of the advancement mechanism and a catheter.

As shown in FIGS. 1 and 2, the advancement mechanism 10 includes, sequentially from the distal end of the sensor assembly cable 111, a cap 13, a sliding inner hypotube 14, a sliding middle tube 15, and a sensor assembly body 16. The sensor assembly body includes an outer tube 17 and a Y-body 18 connected distal of the outer tube. The Y-body 18 includes a side port 19 connected to a fluid line 57 for the infusion of fluids into the Y-body, a rotating locking member 20 having finger grooves 21 for attaching the Y-body to the catheter hub 22, and a unique male luer-type fitting 23 for selective connection to a catheter having a unique female luer-type fitting 24 of complimentary dimensions in the catheter hub.

Figure 4:
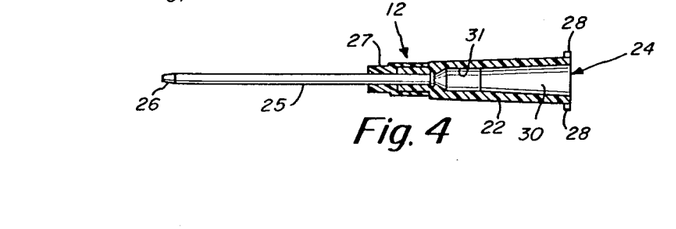
FIG. 4 is an enlarged side, sectional view of the catheter of FIG. 2.

As shown in FIGS. 2 and 4, the catheter 12 consists of a Teflon sheath 25 positionable in the blood vessel and having a tapered distal end 26, a strain relief portion 27, and a hub 22 at its proximal end. The strain relief portion 27 is made of a soft plastic to reduce kinking of the more rigid, thin wall Teflon sheath 25. The hub 22 is made of a rigid molded plastic and includes a pair of outer locking tabs or threads 28 at the proximal end. The locking tabs or threads 28 are rotated into threads 58 provided on the inner bore of the rotating locking member 20 adjacent the distal end of the Y-body. The hub has an inner proximal bore comprising the unique female luer fitting 24 to accomplish a flow-through connection with the advancement mechanism 10 via male connector 23.

Figure 3:
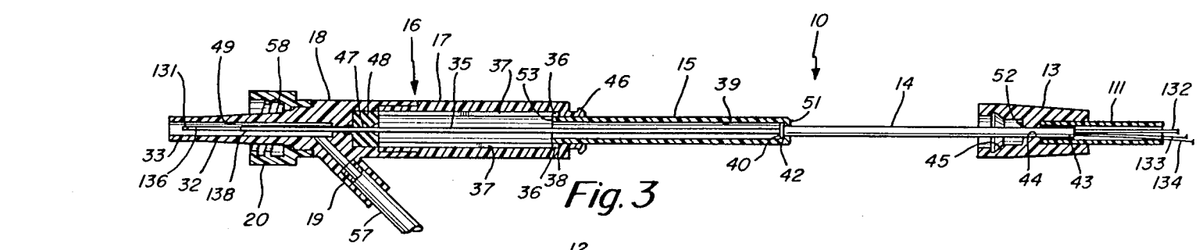
FIG. 3 is an enlarged side, sectional view of the advancement mechanism of FIG. 2.
Figure 9:
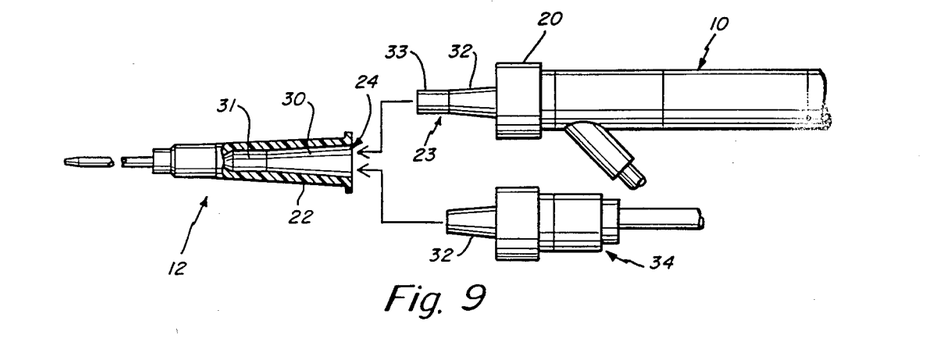
FIG. 9 is a side elevational view, partially in section, of a catheter having a unique female luer-type fitting for use with either a probe advancement mechanism having a unique male luer-type fitting or another device having a standard male luer fitting.

As best shown in FIG. 4, the unique female fitting 24 in the catheter hub 22 consists of a standard tapered female luer fitting 30 at the proximal end of the hub with an additional cylindrical bore 31 extending distally from the standard female luer. As shown in FIG. 3, at the distal end of the Y-body 18 there is provided a standard tapered male luer fitting 32 and distally thereof a cylindrical extension 33 which are dimensioned to slidably engage the tapered luer fitting 30 and bore 31 respectfully of the female fitting in the catheter hub (see FIG. 5). As best shown in FIG. 9, the unique female fitting 24 in the catheter hub 22 permits connection to the catheter hub of any device 34 having a standard male luer fitting 32 or the advancement mechanism 10 having the unique male luer-type fitting 23, but prevents attachment of a catheter not having the unique female luer-type fitting with the probe advancement mechanism 10 of this invention having the unique male luer-type fitting 23. This is required so that the advancement mechanism is used only with catheters having a selected length so that the advancement mechanism positions the distal tip of the probe a predetermined distance from the distal tip of the catheter.

The telescoping elements of the advancement mechanism are best shown in FIGS. 2–3 and 5–7. The advancement mechanism 10 includes a plurality of telescoping elements, including an outer tube 17, a sliding middle tube 15, and a sliding inner hypotube 14. The rigid plastic outer tube 17 has an axial bore 35 in which the rigid plastic middle tube 15 is slidably movable (see FIG. 7). A pair of diametrically-opposed ears 36 at the distal end of the middle tube slide within a pair of diametrically-opposed channels 37 in outer tube 17. Ears 6 engage reduced-diameter ledge 38 at the proximal end of bore 35 so as to retain the distal end of the middle tube within the axial bore 35 of the outer tube when the middle tube is fully retracted from the outer tube see FIG. 3). In FIG. 3, the probe is positioned in the advancement mechanism 10 so that the PO₂ sensor 131 at the distal tip of the probe is positioned within and protected by the Y-body 18.

The middle tube 15 has an axial bore 39 in which the inner metal hypotube 14 is slidably movable. An enlarged diameter lip 40 at the distal end of the hypotube engages a reduced-diameter ledge 42 at the proximal end of bore 39 so as to retain the distal end of hypotube 14 in middle tube 15 when the hypotube is fully retracted from the middle tube (see FIG. 3).

Figure 5:
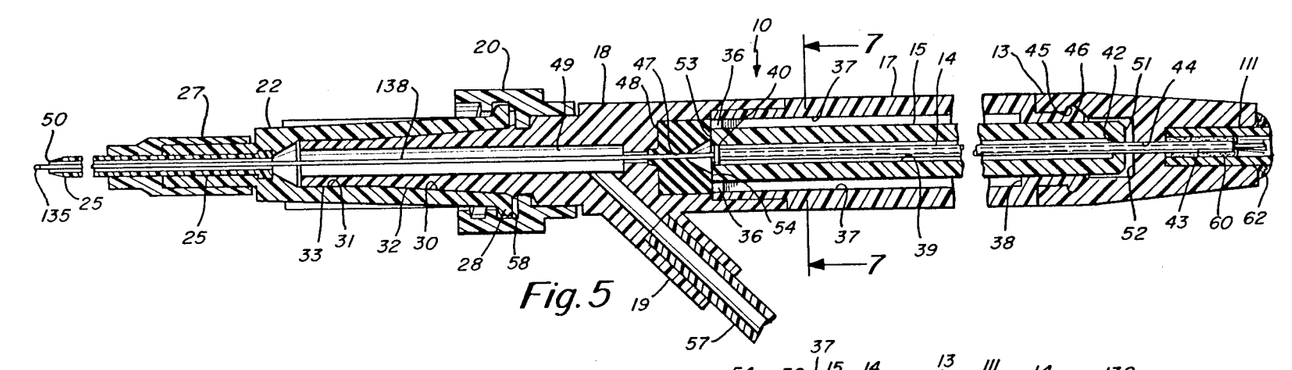
FIG. 5 is a further enlarged side, sectional view of the advancement mechanism and catheter with the probe fully advanced through the catheter.
Figure 6:
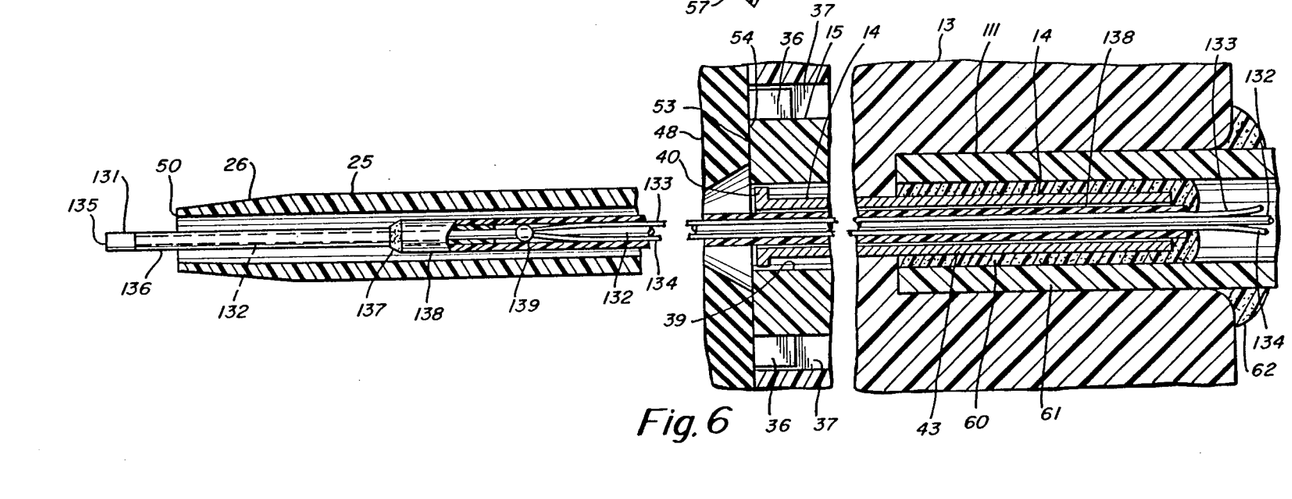
FIG. 6 is a further enlarged side, sectional view of the advancement mechanism and catheter with the probe fully advanced, and showing the thermocouple positioned within the catheter.
Figure 7:
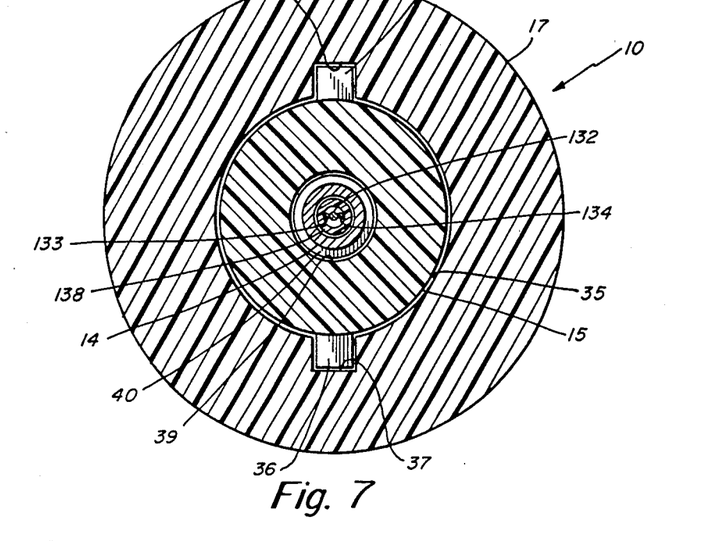
FIG. 7 is a rear, sectional view taken along the section lines 7—7 in FIG. 5.

As shown in FIGS. 5-6, the proximal end 43 of the hypotube 14 is bonded with an adhesive 60 to the distal end 61 of the sensor assembly cable 111 which in turn is bonded by adhesive 62 to the strain relief cap 13. Adhesive 60 further bonds together the proximal end of hypotube 14, the proximal end of polyimide tube 138, and the optical fiber 132 and pair of thermocouple wires 133, 134 at the point they exit from the proximal end of tube 138.

The flexible polymer strain relief cap 13 has an axial bore 44 in which the hypotube 14 is positioned. At the distal end of the cap is an inner locking groove 45 which can be releasably friction-fit over a complimentary shaped locking projection 46 on the proximal end of the outer tube 17 when the telescoping elements are fully collapsed, as shown in FIG. 5. Extending proximal from the cap is the sensor assembly cable 111 in which the optic fiber 132 and two thermocouple wires 133, 134 of the sensor probe are contained and connected via connector cable 110 to the monitor 100.

As shown in FIG. 3, when the telescoping elements are fully expanded, the distal tip of the sensor probe 131 is positioned within the Y-body 18. This is to protect the sensor tip from breakage and prevent contact with a non-sterile surface. The middle tube 15 is retracted proximally of the outer tube 17 and the inner hypotube 14 is retracted proximally of the middle tube 15. The optical fiber 132 extends through each of the telescoping elements and through a central bore 47 of a rubber-type fluid seal 48 provided between bore 35 of outer tube 17 and fluid channel 49 of Y-body 18. This seal permits slidable movement of the optical fiber 132 therethrough but prevents fluids in channel 49 of the Y-body from traveling back into the telescoping elements.

In FIG. 5, the telescoping elements are shown fully collapsed so as to position the distal end 135 of the probe a predetermined distance beyond the distal tip 50 of the catheter. The middle tube 15 and inner hypotube 14 have each been pushed fully forward towards the distal end 50 of the catheter so as to reside within the outer tube 17. The telescoping elements are thus collapsed by the user grasping locking member 20 in one hand and the cap 13 in the other hand and pushing cap 13 forward towards the distal end of the catheter. Because of the joint bonding of cap 13, sensor assembly cable 111, hypotube 14, polyimide tube 138, and optical fiber 132 and thermocouple wires 133 and 134 (see FIG. 6), this action pushes the hypotube and probe forward. In pushing the cap 13 forward, the proximal end 51 of the middle tube 15 eventually engages the wall 52 at the proximal end of the locking bore 45 in the cap so that further forward movement of the cap pushes the middle tube 15 into the outer tube 17 (The slight gap shown in FIG. 5 between elements 51 and 52 is present to allow for tolerance differences in the molded parts.) Forward movement of the telescoping elements and therefore of the probe is stopped when the distal end 53 of the middle tube engages the proximal wall 54 of the seal 48 and the locking projection 46 on the outer tube engages the locking groove 45 in the cap. These stop limits therefore define the predetermined position of the distal tip 135 of the sensor with respect to the distal tip 50 of the catheter when the telescoping elements are fully collapsed.

FIG. 6 is a further enlarged cross-sectional view of the fully-advanced sensor. The sensor tip extends a short distance outside the distal tip of the catheter. The optical fiber 132 is covered by a polyimide tube 136 at its distal end to strengthen the fiber. At a position along the fiber within the catheter there is a step-up 137 to a larger diameter polyimide tube 138. A thermocouple 139 is positioned in an aperture in this larger diameter tube 138 within the catheter sheath 25 for taking the temperature measurement of the fluid in the catheter. Because of the slow infusion rates (e.g., 3–5 cc/hour), the infusion fluid is at body temperature and therefore the temperature being measured is representative of the body. Also, positioning the thermocouple within sheath 25 reduces the surface area exposed to blood and thus reduces the possibility of clotting. Both the thermocouple wires 133, 134 and the optic fiber 132 extend through the larger diameter polyimide tube 138. At its proximal end, the polyimide tube 138 is attached by adhesive 60 to the hypotube 14, sensor assembly cable 111, fiber 132 and thermocouple wires 133 and 134.

One method of use of the apparatus of this invention to position a fiber optic probe in vivo will now be described. The lower forearm of the patient is secured to a rigid board. The radial artery (see FIG. 8) is located just proximal to the head of the radius, and cleaned with an antiseptic. The area is draped with sterile towels. After administering a local anesthetic if the patient is awake, an incision is made at the point of catheter insertion to facilitate entry and minimize trauma to the catheter sheath 25. A needle is inserted at a 30° angle to the surface of the skin and the catheter and needle stylet are gently advanced into the artery until blood appears in the hub of the needle. While holding the needle in a fixed position, the intra-arterial catheter 12 is advanced over the needle and into the artery. The needle is removed while stabilizing the sheath 25 in place.

Figure 8:
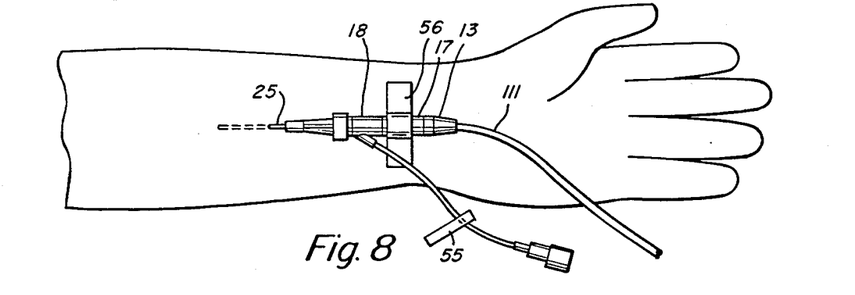
FIG. 8 is a top perspective view of the advancement mechanism taped to the patient's forearm after insertion of the probe into the radial artery.

The sensor system is checked to make sure that the probe is fully retracted within the sensor assembly body (as in FIG. 3) and that the slide clamp 55 on fluid line 57 is open. The male luer connector 23 on Y-body 18 is connected to the female luer connector 24 on catheter hub 22. The threaded connection between locking members 20 and 28 is tightened. The side port 19 is aspirated and flushed. The probe is advanced into the bloodstream by sliding the strain relief cap 13 forward until the cap groove 45 snaps firmly in place over locking projection 46 on outer tube 17. To help maintain patency, a continuous stream of an appropriate flush solution, under pressure, is used. The intraarterial catheter 12 is secured in place. The sensor assembly cable 111 is attached to the patient via connector cable 110. The board may be removed from the forearm and an antimicrobial ointment applied to the site of insertion and covered with a sterile dressing. The sensor assembly body is held down by tape 56 to the patient's forearm, as shown in FIG. 8.

One of the benefits of the apparatus of this invention is the compact profile of the advancement mechanism 10 once the probe is positioned in the body. The advancement mechanism can be taped down to the patient and its small size prevents it from being hit or knocked out of position which potentially could dislodge or move the probe.

A further benefit of the advancement mechanism is that the probe tip is protected and maintained in a sterile environment during insertion.

In making the blood oxygen measurement, the probe tip is positioned a short distance, such as 0.050 inch, beyond the distal tip of the catheter. With the probe and catheter thus directed into the blood flow, the blood washes away the infusion fluid exiting from the catheter tip so that the sensor measures the oxygen concentration in the blood as opposed to the oxygen concentration in the infusion fluid. Furthermore, by positioning the sensor tip a very short distance from the catheter tip, the sensor is less likely to be broken or to injure the blood vessel wall.

While a preferred embodiment of the invention has hereinbefore been described, it is appreciated that variations thereof will be perceived by those skilled in the art, which variations are nevertheless within the scope of the invention as defined by the claims appended hereto.

I claim:

1. Apparatus for axially moving probe, having proximal and distal ends, within a catheter of selected length, having proximal and distal ends, so as to position the distal end of the probe a predetermined distance from the distal end of the catheter, said apparatus comprising:
    telescopic advancement means having proximal and distal ends and engaging the probe for moving the probe axially within the catheter, said telescopic advancement means comprising:
    means for connecting the distal end of said telescopic advancement means to the proximal end of the catheter so as to permit axial movement of the probe within the catheter;
        a plurality of elements connected in telescoping relationship to one another for advancing the probe into the catheter when said telescoping elements are collapsed and for retracting the probe from the catheter when said telescoping elements are expanded and thereby changing the axial length of the advancement means;
        stop means for limiting the relative telescoping movement of said elements so as to position the distal end of the probe a predetermined distance from the distal end of the catheter when the probe is advanced; and
        shielding means for protecting the probe from breakage when the probe is retracted within said telescopic advancement means.

2. The apparatus of claim 1, further comprising a fitting on the distal end of the telescopic advancement means adapted to selectively engage a complimentary dimensioned fitting on the proximal end of the catheter.

3. The apparatus of claim 1, wherein said telescopic advancement means includes a Y-body at its distal end having an axial bore through which the probe is axially movable, a port for the infusion of fluids into the axial bore, and a fluid seal at the proximal end of the axial bore having an aperture which permits slidable movement of the probe therethrough but prevents the transmission of fluid in the axial bore to the telescoping elements.

4. The apparatus of claim 3, further comprising a fitting on the distal end of the telescopic advancement means adapted to selectively engage a complimentary dimensioned fitting on the proximal end of the catheter.

5. Apparatus for axially moving a probe, having proximal and distal ends, within a catheter of selected length, having proximal and distal ends, so as to position the distal end of the probe a predetermined distance from the distal end of the catheter, said apparatus comprising:
    a plurality of elements connected in telescoping relationship to one another for advancing the probe into the catheter when said telescoping elements are collapsed and for retracting the probe from the catheter when said telescoping elements are expanded, said telescoping elements comprising:
    an outer tube having proximal and distal ends and an axial bore extending therethrough;
    means for connecting the distal end of said outer tube to the proximal end of the catheter;
    an inner tube having proximal and distal ends and an axial bore extending therethrough, said inner tube bore being sized to permit axial movement of the probe therethrough, the outer diameter of said inner tube being sized to permit axial movement of said inner tube through said outer tube bore;
    stop means for limiting the distance said inner tube is advanced within sand retracted from said outer tube bore; and
    means for connecting said inner tube to the probe at a predetermined location on the probe so as to position the distal end of said probe at a predetermined position with respect to the distal end of the catheter when said inner tube is fully advanced within said outer tube bore and to position the distal end of said probe within said telescoping elements when said inner tube is fully retracted from said outer tube bore.

6. The apparatus of claim 5, wherein said inner tube comprises:
    a first tube axially movable within said outer tube bore and having a first tube bore extending axially therethrough;
    a second tube axially movable within said first tube bore and having a second tube bore extending axially therethrough, said second tube bore being sized to permit axial movement of the probe therethrough; and
    a cap connected to the second tube and having means for releasably engaging said outer tube when said telescoping elements are collapsed.

7. Apparatus of claim 6, wherein the connecting means at the distal end of the outer tube includes a fitting adapted to selectively engage a complimentary dimensioned fitting on the proximal end of the catheter.

8. The apparatus of claim 7, wherein the connecting means at the distal end of the outer tube includes a Y-body having an axial bore through which the probe is axially movable, a port for the infusion of fluids into the axial bore, and a fluid seal at the proximal end of the axial bore having an aperture which permits slidable movement of the probe therethrough but prevents the transmission of fluid in the axial bore to the telescoping elements.

9. A system for in-vivo positioning of a probe, said system comprising:

a catheter of selected length having proximal and distal ends;

an advancement means for axially moving a probe within said catheter so as to position a distal end of the probe a predetermined distance from the distal end of the catheter; and mating interconnection means permitting selective engagement of the catheter and advancement means.

10. The system of claim 9, wherein said advancement means comprises:

means for connecting the advancement means to the probe at a predetermined location on the probe;

means for connecting the advancement means to the proximal end of the catheter so as to permit axial movement of the probe within the catheter;

means for advancing the probe into the catheter and for retracting the probe from the catheter;

stop means for limiting the movement of the probe in the catheter so as to position the distal end of the probe a predetermined distance from the distal end of the catheter when the probe is advanced; and shielding means for protecting the probe from breakage when the probe is retracted within said advancement means.

11. The system of claim 9, wherein said mating interconnection means comprises a female fitting at the proximal end of the catheter and a complimentary dimensioned male fitting at the distal end of the advancement means, said female fitting comprising a female tapered luer fitting at the proximal end of the catheter and distally thereof a cylindrical bore, and said male fitting comprises a male tapered luer fitting and distally thereof a cylindrical projection each dimensioned for slidable engagement within the female luer fitting and cylindrical bore respectively.

* * * * *

UNITED STATES PATENT AND TRADEMARK OFFICE
CERTIFICATE OF CORRECTION

PATENT NO. : 4,795,434
DATED : January 3, 1989
INVENTOR(S) : Kujawski

It is certified that error appears in the above—identified patent and that said Letters Patent is hereby corrected as shown below:

Col.2 , line 16 -  change "for" to -- from --.

Col.1 , line 22 -  change "patient s" to -- patient's --.

Col.4 , line 66 -  change "6" to -- 36 --.

Col.5 , line 2 -  before "see" insert -- ( --.

Col.7 , line 27 -  before "probe" insert -- a --.

Col. 8, line 30 -  change "sand" to -- and --.

Signed and Sealed this

Twenty-third Day of May, 1989

Attest:

DONALD J. QUIGG

Attesting Officer

Commissioner of Patents and Trademarks